US006248553B1

(12) United States Patent
Small et al.

(10) Patent No.: US 6,248,553 B1
(45) Date of Patent: Jun. 19, 2001

(54) ENZYME METHOD FOR DETECTING LYSOPHOSPHOLIPIDS AND PHOSPHOLIPIDS AND FOR DETECTING AND CORRELATING CONDITIONS ASSOCIATED WITH ALTERED LEVELS OF LYSOPHOSPHOLIPIDS

(75) Inventors: Christopher L. Small; Jeff A. Parrott; Liang Zhong Xu, all of Pullman, WA (US)

(73) Assignee: Atairgin Technologies, Inc., Irvine, CA (US)

( * ) Notice: Subject to any disclaimer, the term of this patent is extended or adjusted under 35 U.S.C. 154(b) by 0 days.

(21) Appl. No.: 09/176,813

(22) Filed: Oct. 22, 1998

(51) Int. Cl.[7] ............... C12Q 1/26; C12Q 1/32; C12Q 1/48; C12Q 1/61
(52) U.S. Cl. ............... 435/25; 435/26; 435/15; 436/71
(58) Field of Search ............... 435/18, 25, 15, 435/26; 554/78, 80; 436/13, 71

(56) References Cited

U.S. PATENT DOCUMENTS

| 4,693,971 | 9/1987 | Misaki ................ 435/17 |
| 4,698,299 | 10/1987 | Janoff et al. ........... 435/13 |
| 4,784,945 | * 11/1988 | Artiss et al. ........... 435/25 |
| 5,122,454 | 6/1992 | Ueda et al. ............ 435/15 |
| 5,277,917 | 1/1994 | Xu et al. .............. 424/537 |
| 5,326,690 | 7/1994 | Xu et al. .............. 435/29 |
| 5,489,580 | 2/1996 | Makriyannis et al. ...... 514/101 |

FOREIGN PATENT DOCUMENTS

| 882.048 | 9/1980 | (BE) . |
| 210691 | 3/1997 | (DE) . |
| 0 322 262 | 6/1989 | (EP) ............... C07K/13/00 |
| 63-13644 | 1/1988 | (JP) ............... B22C/9/00 |
| 2-107195 | 4/1990 | (JP) ............... C12P/9/10 |
| 8-53475 | 2/1996 | (JP) ............... C07F/9/10 |
| WO 89/01773 | 3/1989 | (WO) .............. A61K/9/20 |
| WO 90/10448 | 9/1990 | (WO) .............. A61K/31/70 |
| WO 93/11136 | 6/1993 | (WO) .............. C07F/9/165 |
| WO97/45727 | 4/1997 | (WO) .............. G01N/33/48 |

OTHER PUBLICATIONS

Fleming et al. Assessment of phosphatidylcholine, lysophosphatidylcholine, and sphingelomyelin in human serum. Clinical Biochemistry, 20 (4), pp. 249–256. (Aug. 1987).*
Lehninger. Biochemistry, 2nd edition. pp. 290–291. Worth Publishers, Inc. New York. (1975). No month found.*
Domansky, V., (1992) "Functional Condition and Phospholipid Profile of Red Blood Cells in Breast Cancer Patients," Vopr. Onkol. 38(10): 1194–1202.
Kalnova, N.Yu, (1989), "Relationship Between Antioxidant Activity and Blood Lipid Profile As a Marker of Tumor Effect on the Host," Vopr. Onkol. 35(7):785–801.

Asaoka et al., "Role of lysophosphatidylcholine in T–lymphocyte activation: Involvement of phospholipase $A_2$ in signal transduction through protein kinase C," Proc. Natl. Acad. Sci. USA 89:6447–6451 (Jul. 1992).
Asaoka et al., "Potential role of phospholipase $A_2$ in HL–60 cell differentiation to macrophages induced by protein kinase C activation," Proc. Natl. Acad. Sci. USA 90:4917–4921 (Jun. 1993).
Bligh and Dyer, "A rapid method of total lipid extraction and purification," Can. J. Biochem. Physiol. 37(8):911–917 (Aug. 1959).
Bowes et al., "The Acquisition of Lysophosphatidylcholine by African Trypanosomes," J. Biol. Chem. 268(19):13885–13892 (Jul. 1993).
Creer and Gross, (1985), "Separation of Isomeric Lysophospholipids by Reverse Phase HPLC," Lipids 20(12):922–928.
Dorum et al., (1996), "Early detection of familial ovarian cancer," E. J. Cancer 32A(10): 1645–1651.
Einhorn et al., (1992), "Prospective evaluation of serum CA 125 levels for early detection of ovarian cancer," Obstet. Gynecol. 80:14–18.
Fukami et al., "Antibody to phosphatidylinositol 4,5–bisphosphate inhibits oncogene–induced mitogenesis," Proc. Nat'l. Acad. Sci. USA 85:9057–9061 (Dec. 1988).
Gaudette et al., "Mass and fatty acid composition of the 3–phosphorylated phosphatidylinositol bisphosphate isomer in stimulated human platelets," J. Biol. Chem. 268(19):13773–13776 (Jul. 1993).
Gillett et al., (1975), "Plasma concentrations of lysolecithin and other phospholipids in the healthy population and in men suffering from atherosclerotic diseases," Atherosclerosis 22:111–124.
Gregor Cevc, ed., Phospholipids Handbook, Ch. 28: Gupta, "Phospholipids in Disease," pp. 895–908, 1993.
Hara et al., (1996), "Lysophosphatidylserine Enhances Exogenous Type II Phospholipase $A_2$–Induced Activation of Rat Serosal Mast Cells," Biol. Pharm. Bull. 19(3):474–476.
Higashiyama et al., "A Heparin–Binding Growth Factor Secreted by Macrophage–Like Cells That Is Related to EGF," Science 251:936–939 (Feb. 1991).
Jacobs et al., (1988), "Multimodal approach to screening for ovarian cancer," Lancet Feb. 6, 1988 268–271.

(List continued on next page.)

Primary Examiner—Ardin H. Marschel
Assistant Examiner—Marjorie A. Moran
(74) Attorney, Agent, or Firm—Lyon & Lyon LLP

(57) ABSTRACT

The present invention is an enzymatic method and diagnostic kits for detecting and quantifying the presence of one or more lysophospholids in a sample of bodily fluid taken from a test subject. The method uses enzymes in a two step assay and may be used to detect disease conditions associated with altered levels of lysophospholipids and to correlate such conditions with altered levels of lysophospholipids.

20 Claims, No Drawings

OTHER PUBLICATIONS

Jacobs et al., "Risk of diagnosis of ovarian cancer after raised serum CA 125 concentration: a prospective cohort study," *BMJ* 313:1355–1358 (Nov. 1996).

Jalink et al., (1994), "Growth factor–like effects of lysophosphatidic acid, a novel lipid mediator," *Biochim. Biophys. Acta* 1198:185–196.

Kawasaki et al., (1989), "Determination of Inorganic Phosphate by Flow Injection Method with Immobilized Enzymes and Chemiluminescence Detection," *Analytical Biochem.* 182:366–370.

Keating et al., (1996), "Inhibition of protein synthesis in frog (*Xenopus laevis*) egg extracts by an antibody against phosphatidylinositol 4,5–bisphosphate," *Biochem. J.* 317(3):643–646.

Kriat et al., (1993), "Analysis of plasma lipids by NMR spectroscopy: Application to modifications induced by malignant tumors," *J. Lipid Res.* 34:1009–1019.

Kume and Gimbrone, (1994), "Lysophosphatidylcholine transcriptionally induces growth factor gene expression in cultured human endothelial cells," *J. Clin. Invest.* 93:907–911.

Lloret and Moreno, (1995), "$Ca^{2+}$ Influx, Phosphoinositide Hydrolysis, and Histamine Release Induced by Lysophosphatidylserine in Mast Cells," *J. Cell Physiol.* 165:89–95.

Lloret and Moreno, (1994), "Immunochemical relatedness between secretory phospholipase $A_2$ and intracellular phospholipase $A_2$ activity linked with arachidonic acid mobilization in macrophages," *Toxicon* 32(11):1327–1336.

Matuoka et al., "Mitogenesis in response to PDGF and bombesin abolished by microinjection of antibody to $PIP_2$," *Science* 239:640–643 (Feb. 1988).

Mills et al., "A putative new growth factor in ascitic fluid from ovarian cancer patients: Identification, characterization, and mechanism of action," *Cancer Research* 48:1066–1071 (Mar. 1988).

Mills et al., "Ascitic fluid from human ovarian cancer patients contains growth factors necessary for intraperitoneal growth of human ovarian adenocarcinoma cells" *J. Clin. Invest.* 86:851–855 (Sep. 1990).

Moolenaar, (1995), "Lysophosphatidic acid signalling," *Current Opinion in Cell Biol.* 7:203–210.

Moolenaar, "Lysophosphatidic acid, a multifunctional phospholipid messenger," *J. Biol. Chem.* 270(22):12949–12952 (Jun. 1995).

Moolenaar et al., (1992), "Lysophosphatidic acid: A bioactive phospholipid with growth factor–like properties," *Rev. Physiol. Biochem. Pharmacol.* 119:47–65.

Muto et al., (1993), "Screening for Ovarian Cancer: The preliminary experience of a familial ovarian cancer center," *Gynecologic Oncol.* 51:12–20.

Nakano et al., "Lysophosphatidylcholine upregulates the level of heparin–binding epidermal growth factor–like growth factor mRNA in human monocytes," *Proc. Natl. Acad. Sci. USA* 91:1069–1073 (Apr. 1994).

Ogawa, (1997), "Group II Phospholipase $A_2$ in Neoplastic Disease," In: *Phospholipase A: Basic and Clinical Aspects in Inflammatory Diseases*, Uhl, et al. Eds. vol. 24, pp. 200–204.

Okita et al., (1997), "Elevated levels and altered fatty acid composition of plasma lysophosphatidylcholine (LYSOPC) in ovarian cancer patients," *Int. J. Cancer* 71:31–34.

Panetti et al., (1997), "Endothelial cell mitogenesis induced by LPA: Inhibition by thrombospondin–1 and thrombospondin–2," *J. Lab. Clin. Med.* 129:208–216.

Phillips and Dodge, (1967), "Composition of phospholipids and of phospholipid fatty acids of human plasma," *J. Lipid Res.* 8:676–681.

Racenis et al., (Sep. 1992), "The Acyl Dihydroxyacetone Phosphate Pathway Enzymes for Glycerolipid Biosynthesis are Present in the Yeast *Saccharomyces cerevisiae*," *J. Bacteriol.* 174:5702–5710.

Resnick and Tomaska, "Stimulation of Yeast Adenylyl Cyclase Activity by Lysophospolipds and Fatty Acids," *J. Biol. Chem.* 269(51):32336–32341 (Dec.1994).

Ross, "The pathogenesis of atherosclerosis: A perspective for the 1990s," *Nature (London)* 362:801–809 (Apr. 1993).

Sasaki et al., "Potentiation of diacylglycerol–induced activation of protein kinase C by lysophospholipids," *FEBS Letters* 320(1):47–51 (Mar. 1993).

Schapira et al., (1993), "The effectiveness of ovarian cancer screening: A decision analysis model," *Ann. Intern. Med.* 118:838–843.

Schrier et al., "The Effects of the Phospholipase $A_2$ Inhibitor, Manoalide, on Cartilage Degradation, Stromelysin Expression, and Synovial Fluid Cell Count Induced by Intraarticular Injection of Human Recombinant Interleukin–1α in the Rabbit," *Arthritis Rheum.* 39(8):1292–1299 (Aug. 1996).

Shen, et al., "Evaluation of lysophosphatidic acid (LPA) as a diagnostic marker for ovarian cancer and other gynecological cancers," *Clinical Chemistry* 43:(6):577 (Jul. 1997).

Skeaff and Holub, (1987), "Effect of dietary fish oil containing eicosapentaenoic acid on the fatty acid composition of platelet phospholipids and on the thrombin–stimulated phospholipid alterations in human platelets," *Colloque INSERM* 152:63–76.

Skipski et al., (1967), "Lipid composition of human serum lipoproteins," *Biochem. J.* 104:340–352.

Steinberg et al., "Beyond cholesterol: Modifications of low–density lipoprotein that increase its atherogenicity," *N. Eng. J. Med.* 320(14):915–924 (Apr. 1989).

Tamori–Natori et al., (1986), "Metabolism of Lysophosphatidylserine, a Potentiator of Histamine Release in Rat Mast Cells," *J. Biochem. (Tokyo)* 100(3):581–590.

Thomas and Holub, (1991), "Eicosanoid–dependent and–independent formation of individual [$^{14}C$]stearoyl–labeled lysophospholipids in collagen–stimulated human platelets," *Biochim. Biophys. Acta* 1081:92–98.

Tigyi et al., "Lysophosphatidic acid possesses dual action in cell proliferation," *Proc. Natl. Acad. Sci. USA* 91:1908–1912. (Mar. 1994).

Tokumura et al., (1986), "Involvement of lysophospholipase D in the production of lysophosphatidic acid in rat plasma," *Biochim. Biophys. Acta* 875:31–38.

Tramposch et al., (1994), "Inhibitor of Phospholipase $A_2$ Blocks Eicosanoid and Platelet Activating Factor Biosynthesis and Has Topical Anti–Inflammatory Activity," *The Journal of Pharmacology and Experimental Therapeutics* 271(2):852–859.

Van den Bosch et al., 1974, "Phosphoglyceride Metabolism," *Ann. Rev. Biochem.* 43:243–277.

Vogt, 1960, "Darmerregende Aktivität verschiedener Phosphatide und Glykolipide," *Arch. exp. Path. u. Pharmak.* 240:134–139.

Xu et al., (1995), "Lysophospholipids activate ovarian and breast cancer cells," *Biochem. J.* 309:933–940.

Xu et al., "Characterization of an ovarian cancer activating factor in ascites from ovarian cancer patients[1]," *Clin. Cancer Res. 1*:1223–1232 (Oct. 1995).

Xu et al, (1995), "Effect of Lysophospholipids on Signaling in the Human Jurkat T Cell Line" *J Cell Physiol 163*: 441–450.

Yoshida et al., "Platelet activation by simultaneous actions of diacylglycerol and unsaturated fatty acids," *Proc. Natl. Acad. Sci. USA 89*:6443–6446, (Jul. 1992).

* cited by examiner

ENZYME METHOD FOR DETECTING LYSOPHOSPHOLIPIDS AND PHOSPHOLIPIDS AND FOR DETECTING AND CORRELATING CONDITIONS ASSOCIATED WITH ALTERED LEVELS OF LYSOPHOSPHOLIPIDS

1. FIELD OF THE INVENTION

The present invention relates to enzyme methods for detecting lysophospholipids, such as lysophosphatidic acid, (LysoPA) and lysophosphatidyl choline (LysoPC), in biological fluids, and for correlating and detecting conditions associated with altered levels of lysophospholipids.

2. BACKGROUND OF THE INVENTION

Phosphatidyl choline (PC), also named lecithin, is one of the major sources of polyunsaturated fatty acids such as arachidonic and linoleic acids. The former is a precursor of eicosanoids which have numerous biological activities. Hydrolysis of PC yields lysophosphatidyl choline (LysoPC) and constituent fatty acids, which have been implicated in signal transduction (Asaoka et al., *Proc. Natl. Acad. Sci. USA* 90:4917–4921 (1993); Yoshida et al., *Proc. Nati. Acad. Sci. USA* 89:6443–6446 (1992)). An increasing body of evidence indicates that LysoPC, which is present in high concentrations in oxidized low density lipoproteins may play a significant role in atherogenesis and other inflammatory disorders (Steinberg et al., *New. Eng. J. Med.* 320:915–924 (1989)). LysoPC has been reported to increase the transcription of genes encoding platelet derived growth factor A and B chains, and heparin-binding epidermal growth factor-like protein (HB-EGF) in cultured endothelial cells (Kume and Gimbrone, *J. Clin. Invest.* 93:907–911 (1994)), and to increase mRNA encoding HB-EGF in human monocytes (Nakano et al., *Proc. Natl. Acad. Sci. USA* 91:1069–1073 (1994)). These gene products are mitogens for smooth muscle cells and fibroblasts (Higashiyama et al., *Science* 251:936–939 (1991); Ross, *Nature* (Lond.) 362:801–809 (1993)). LysoPC has also been shown to activate protein kinase C in vitro (Sasaki et al., *FEBS Letter* 320:47–51 (1993)), to potentiate the activation of human T lymphocytes (Asaoka et al., *Proc. Natl. Acad. Sci. USA* 89:6447–6451 (1992)) and to potentiate the differentiation of HL-60 cells to macrophages induced by either membrane-permeable diacylglycerols or phorbol esters (Asaoka et al., *Proc. Natl. Acad. Sci. USA* 90:4917–4921 (1993)).

LysoPC may also provide a source of bioactive lysophosphatidic acid (1-acyl-sn-glycero-3-phosphate, LysoPA) (Moolenaar et al., *Rev. Physiol. Biochem. Pharmacol.* 119:47–65 (1992)) through hydrolysis by lysophospholipase D (Tokumara et al., *Biochim. Biophys. Acta* 875:31–38 (1986)). LysoPA is a naturally occurring phospholipid with a wide range of growth factor-like biological activities. It is well established that LysoPA can act as a precursor of phospholipid biosynthesis in both eukaryotic and prokaryotic cells (Van den Bosch, *Ann. Rev. Biochem.* 43:243–277 (1974); Racenis et al., *J. Bacteriol.* 174:5702–5710 (1992)). The ability of LysoPA to act as an intercellular lipid mediator has been noted (Vogt, *Arch. Pathol. Pharnakol.* 240:124–139 (1960); Xu et al., *J. Cell. Physiol.* 163:441–450 (1995); Xu et al., *Biochemistry* 309:933–940 (1995); Tigyi et al., Cell Biol. 91:1908–1912 (1994); Panetti et al., *J. Lab. Clin. Med.* 129(2):208–216 (1997)). LysoPA is rapidly generated by activated platelets and can stimulate platelet aggregation and wound repair.

Ovarian cancer activating factor (OCAF), has been isolated from ovarian cancer ascites fluid (Mills et al., *Cancer Res.* 48:1066 (1988); Mills et al. *J. Clin. Invest.* 86:851 (1990) and U.S. Pat. Nos. 5,326,690 and 5,277,917) and has been identified to consist of multiple forms of LysoPA (Xu et al., *Clin. Cancer Res.* 1:1223–1232 (1995)). LysoPA has been identified as a potent tumor growth factor in the ascites fluid of ovarian cancer patients (Id.)

Other lysophospholipids associated with various conditions include lysophosphatidyl serine (LysoPS), lysophosphatidyl ethanolamine (LysoPE), lysophosphatidyl glycerol (LysoPG and lysophosphatidyl inositol (LysoPI). Activated platelets secrete two kinds of phospholipase: sPLA2 and PS-PLA1. sPLA2 is reported to be elevated in inflammatory reactions and inhibition of this enzyme reduced inflammation (Schrier et al., *Arthritis Rheum.* 39(8):1292–1299 (1996); Tramposch et al., *Pharmacol. and Experimental Therapeutics* 271(2):852–859 (1994)). PS-PLA1 hydrolyzes phosphatidylserine or lysophosphatidyl serine (LysoPS) specifically to produce LysoPS or Glycerol-3-P serine. LysoPS strongly enhances degranulation of rat mast cells induced by concanavalin A and potentiates histamine release (Tamori-Natori et al., *J. Biochem* (Tokyo) 100(3):581–590 (1986)), and can stimulate sPLA2-elicited histamine release from rat serosal mast cells (Hara et al., *Biol. Pharm. Bull.* 19(3):474–476 (1996)). LysoPS is an inflammatory lipid mediator (Lloret et al., *J. Cell Physiol.* 165(1):89–95 (1995)) and sPLA2 has been implicated in inflammation processes (Lloret et al., *Toxicon* 32(11):1327–1336 (1994)). LysoPI has been shown to stimulate yeast adenylyl cyclase activity with implications for modulating the activity of downstream effector molecules and their interaction with RAS proteins (Resnick and Thomaska, *J. Biol. Chem.* 269(51):32336–32341 (1994)).

Methods for separating and semi-quantitatively measuring phospholipids such as LysoPA using techniques such as thin-layer chromatography (TLC) followed by gas chromatography (GC) and/or mass spectrometry (MS) are known. For example, lipids may be extracted from the test sample of bodily fluid using extraction procedures such as those described by Bligh and Dyer, *Can. J. Biochem. Physiol.* 37:911–917 (1959). Thin-layer chromatography may be used to separate various phospholipids, for example as described by Thomas and Holub, *Biochim. Biophys. Acta*, 1081:92–98 (1991). Phospholipids and lysophospholipids are then visualized on plates, for example using ultraviolet light as described by Gaudette et al., *J. Biol. Chem.* 268:13773–13776 (1993). Alternatively, lysophospholipid concentrations can be identified by NMR or HPLC following isolation from phospholipids or as part of the phospholipid (Creer and Gross, *Lipids* 20(12):922–928 (1985) and Bowes et al., *J. Biol. Chem.* 268(19)13885–13892 (1993)). LysoPA levels have also been determined in ascites from ovarian cancer patients using an assay that relies on LysoPA-specific effects on eukaryotic cells in culture (Mills et al., *Cancer Res.* 48:1066–1071 (1988)). However, these prior procedures are time-consuming, expensive and variable and typically only semi-quantitative.

Development of a rapid and sensitive assay for lysophospholipid species would facilitate use of these lysophospholipids as markers for cellular activities such as platelet activation and for conditions associated with altered levels of lysophospholipid species. Moreover, such assays would provide a method for determining correlations between altered levels of a lysophospholipid and conditions associated with such altered levels.

3. SUMMARY OF THE INVENTION

The present invention encompasses enzymatic methods for determining concentrations of lysophospholipids, such as LysoPA, in samples of biological fluids such as serum or plasma. The methods involves a two-step enzymatic digestion of at least one type of lysophospholipid to produce a substrate for a subsequent enzymatic reaction which produces a detectable end product that then permits detection of the concentration of the lysophospholipid.

The methods are carried out by detecting the concentration of a lysophospholipid such as LysoPA in a sample of bodily fluid taken from a subject. The lysophospholipid in the sample is preferably first enriched through extraction of lipids. For example, polar lipids are redissolved in aqueous solution and the concentration of lysophospholipid is determined using a two-step enzymatic reaction. The lysophospholipid is digested using an enzyme to generate a product that is then subject to a second enzymatic reaction. In a specific embodiment, the second reaction is an enzymatic cycling reaction that amplifies the signal. This method permits measurement of a lysophospholipid present in small amounts in the test sample.

In one embodiment, an enzyme such as lysophospholipase or phospholipase B is used to liberate G3P from LysoPA. The level of G3P is determined using an enzymatic cycling reaction that employs G3P oxidase and glycerol-3-phosphate dehydrogenase in the presence of NADH. The amount of LysoPA detected is quantitated spectrophotometrically by measuring the oxidation of NADH. Alternatively, the amount of LysoPA is determined colorimetrically by detection of hydrogen peroxide generated by the cycling reaction.

In addition to LysoPA, other lysophospholipids such as LysoPC, lysophosphatidyl serine (LysoPS), lysophosphatidyl inositol (LysoPI), lysophosphatidyl ethanolamine (LysoPE) and lysophosphatidyl glycerol (LysoPG), can be detected using the methods of the invention. For these lysophospholipids, alternative enzymes for use in the methods include, but are not limited to, phospholipase $A_1$, phospholipase $A_2$, phospholipase C, phospholipase D, lecithinase B and lysolecithinase, glycerophosphocholine phosphodiesterase and glycerol kinase.

The enzymatic methods of the invention can be used to detect altered levels of lysophospholipid in a subject compared to normal levels of the lysophospholipid in normal to detect conditions associated with such altered levels of lysophospholipid. Diagnosis of a condition using the methods of the invention may also be performed by determining the rate of change over time of the concentration of a lysophospholipid in samples taken from the subject.

Another embodiment of the invention is use of the assay in a method to determine whether a correlation exists between the level of a lysophospholipid and the presence of a condition. In this embodiment, the concentration of a lysophospholipid is determined in samples from subjects known to have a specific disease condition, such as an inflammatory condition, and compared to concentration of that lysophospholipid in subjects free of such condition. Altered levels of lysophospholipid in the samples from the subjects having a condition as compared to samples from normal subjects suggest a correlation between the levels of the lysophospholipid and the presence of the condition.

Yet another embodiment of the methods of the invention is a diagnostic kit containing enzyme and other reagents for conducting the enzymatic assays of the invention to measure concentrations of lysophospholipids in samples of bodily fluids taken from subjects.

5. DETAILED DESCRIPTION OF THE INVENTION

The present invention provides enzymatic methods for detecting and quantifying altered concentrations of lysophospholipids, including, but not limited to, lysophosphatidic acid (LysoPA), lysophosphatidyl choline (LysoPC), lysophophatidyl serine (LysoPS), lysophosphatidyl inositol (LysoPI), lysophosphatidyl ethanolamine (LysoPE) and lysophosphatidyl glycerol (LysoPG) in a sample of bodily fluid from a subject.

The subject is an eukaryotic organism, preferably a vertebrae, including, but not limited to, a mammal, a bird, a fish, an amphibium, or a reptile. Preferably, the subject is a mammal, most preferably a human. The bodily fluid includes, but is not limited to, plasma, serum, urine, saliva, ascites, cerebral spinal fluid or pleural fluid.

The conditions correlated with altered concentrations of these lysophospholipids include, but are not limited to, inflammatory conditions, i.e. conditions associated with platelet activation. Altered phospholipid metabolism has been reported in a number of diseases (for review see Gregor Cevc (Ed.), Phospholipids Handbook, Ch. 28: Gupta, Phospholipids in Disease, pp. 895–908 (1993)) and can lead to altered lysophospholipid and phospholipid levels in biological fluids. These diseases include, but are not limited to, sickle cell anemia, diabetes, muscular dystrophy, ischemia, liver disease, lung disease, heart disease, malaria, Alzheimer's, Parkinson's and various cancers. In these conditions, defective cellular functions may directly or indirectly lead to changes in steady state levels of phospholipids. Other diseases include bleeding disorders including those associated with abnormal platelet function resulting in coagulopathy.

Thus, the methods of the present invention are directed to the detection of conditions that are known to correlate, or the identification of conditions to correlate, with altered concentrations of lysophospholipids in the bodily fluids from a subject relative to concentrations found in bodily fluids from a subject lacking a condition associated with altered concentrations of lysophospholipids (i.e. "normal subjects").

5.1 Uses of the Invention

The methods of the invention provides a rapid and accurate assay with increased sensitivity for detecting small amounts of lysophospholipids present in samples of bodily fluids from subjects. The enzymatic assay can be used to detect conditions associated with altered levels of lysophospholipids in a sample from a subject as compared to normal samples. In addition, the assay permits determination of correlations between various disease conditions and alterations in the levels of lysophospholipids. The methods of the invention and test kits thus provide a practical means to detect conditions associated with altered levels of certain lysophospholipids.

5.2 Enzymatic methods for detecting and quantifying Lysophospholipids

The methods of the invention are carried out as follows. A biological sample such as whole blood is collected from a subject. Lipids are extracted from plasma or serum from the sample, for example, by organic extraction using chloroform:methanol and centrifuigation and enriching for a selected species of lysophospholipid, e.g. LysoPA, or for total lysophospholipids. The need for enrichment depends in part on the specificity of the enzyme used to digest the lysophospholipid to be determined. An enzyme which hydrolyzes the lysophospholipid is incubated with the extracted lipid sample producing a smaller metabolite. Next another enzymatic digestion is performed to produce a detectable product. In one embodiment an enzyme cycling reaction which consists of two enzymatic reactions that accumulates detectable products is performed. In the Examples herein to detect LysoPA levels, Phospholipase B (PLB) or lysophospholipase (LYPL, EC 3.1.1.5, Asahi Chemical Industry Co., Ltd., Tokyo, Japan) is used to produce glycerol-3-phosphate (G-3-P). An enzyme cycling reaction is then performed using glycerol-3-phosphate dehydrogenase, glycerol-3 -phosphate oxidase and NADH to accumlate $H_2O_2$ and NAD (U.S. Pat. No. 5,122,454, Ueda et al.)

The level of LysoPA is detected by monitoring the oxidation of NADH spectrophotometrically at 340 nm (i.e. disappearance of $OD_{340}$) and the accumulation of $H_2O_2$ colorimetrically using peroxidase. Numerical values are obtained from a standard curve consisting of known C18:1 LysoPA. Typical standard curves include known amounts of LysoPA from 0 to 3 $\mu$M. Assays are preferably performed in duplicate with both positive and negative controls. The difference between $OD_{340}$ before and after the enzyme cycling reaction is directly proportional to the amount of LysoPA present. Background signals in plasma without phospholipase B are substracted from all samples. LysoPA standard curve values are plotted and fitted to a linear or second-order polynominal curve fit. The levels of LysoPA in each sample are determined by comparing each signal measured to the standard curve.

Alternatively, the lysophospholipid can be detected using additional and/or different enzyme combinations. For example, phospholipase C (EC 3.1.4.3, Sigma Chemical Co., St. Louis, Mo.) is used to cleave inorganic phosphate (Pi) from LysoPA. Levels of LysoPA are then determined by measuring the amount of liberated Pi using established procedures, e.g. using a commercially available kit (Procedure 670, Sigma Chemical Co., St. Louis, Mo.). For increased sensitivity, Pi is determined using purine nucleoside phosphorylase (PNP), xanthine oxidase (XOD) and urate oxidase (UOD) as previously described (Kawasaki et al., *Analytical Biochem.* 182:366–370 (1989)). The latter method generates 3 $H_2O_2$ molecules for every Pi. The accumulation of $H_2O_2$ is detected colorimetrically using peroxidase.

In another embodiment, the lysophospholipid, such as LysoPA, is incubated with phospholipase B or lysophospholipase to produce G-3-P. G-3-P is converted to dihydroxyacetone phosphate and hydrogen peroxide using G-3-P oxidase in the presence of oxygen and water. In the presence of NADH, G-3-P dehydrogenase converts dihydroxyacetone phosphate back to G-3-P and oxidizes NADH to NAD. The disappearance of NADH is monitored spectrophotometrically at $OD_{340}$. Alternatively, the production of hydrogen peroxide may be measured, for example colorimetrically by fluorometry or chemiluminescence. For a colorimetric assay any of a number of chromogenic substrates may be used including 4-aminoantipyrine (AAP), pyrogallol, 2-(2'-Azinobis (3-ethylbenzthiazoline-sulfonic acid) (ABTS) and 3,3',5,5'-tetramethylbenzidine) (TMB).

In yet another embodiment, LysoPC may be determined by liberating glycerophosphorylcholine (GPC) and fatty acid from LysoPC using phospholipase B or lysophospholipase. The level of LysoPC is determined by liberating choline and glycero-3-phosphate (G-3-P) from GPC using GPC phosphodiesterase (GPC-PDE) followed by a colorimetric enzymatic determination of choline using choline oxidase, 4-aminoantipyrine (AAP), 3,5 Dichloro-2-hydroxybenzenesulfonic acid sodium salt (HDCBS) and peroxidase. Choline is detected by oxidizing to $H_2O_2$ and betaine and then using peroxidase to form quinoneimine dye. Alternatively, G-3-P is measured using G-3-P dehydrogenase and oxidase in the cycling reaction of the assay of the invention.

In addition to LysoPA and LysoPC, other lysophospholipids such as lysophosphatidyl serine (LysoPS), lysophosphatidyl inositol (LysoPI), lysophosphatidyl ethanolamine (LysoPE) and lysophosphatidyl glycerol (LysoPG), can be detected using the two step enzymatic assay methods of the invention.

Enzymes for use in the first step of the method to digest lysophospholipids include, but are not limited to, lysophospholipase, phospholipase B, phospholipase $A_1$, phospholipase $A_2$, phospholipase C, and phospholipase D.

Enzymes for use in detecting the product of enzymatic digestion of lysophospholipids in step one include glycerol-3-phosphate dehydrogenase, glycerol-3-phosphate oxidase, glycerophosphorylcholine phosphodiesterase (GPC-PDE), choline oxidase, serine dehydrogenase, serine deaminase, aldehyde dehydrogenase, ethanolamine deaminase, glycerokinase and glycerol dehydrogenase.

For example, to determine LysoPS, the LysoPS is digested by phospholipase D into serine and LysoPA. The amount of serine produced is determined by detecting NADH formation (absorbance at $A_{340}$) via serine dehydrogenase. Alternatively, the serine is deaminated using deaminase to form ammonia ($NH_3$) and $HOCH_2$—CO—COOH. Alternatively, LysoPS can be digested by lysophospholipase to form Glycerol-3-P serine which is then digested using glycerol-3-P choline phosphodiesterase (GPC-PDE) to form Glycerol-3-P and serine. The LysoPS is determined by detecting $NH_3$ production or NADPH production via serine dehydrogenase or by using a Lyso-PS specific lysophospholipase enzyme.

LysoPE can be determined using the enzyme assay of the invention by hydrolyzing LysoPE into LysoPA and ethanolamine by phospholipase D. The ethanolamine is then deaminated by deaminase and dehydrogenated to produce NADH to produce $HOCH_2$—CHO and $NH_3$ The $HOCH_2$—CHO is then digested with aldehyde dehyrogenase to form NADH which is then detected by spectrometry (e.g. at $A_{340}$). Alternatively a LysoPE-specific lysophospholipase enzyme can be used to hydrolyze LysoPE to Glycerol-3-P ethanolamine which in turn is hydrolyzed to Glycerol-3-P by glycerophosphorylcholine phosphodiesterase (GPC-PDE). Glycerol-3-P is then measured using the cycling reaction of the invention.

In the methods of the invention, an alternative to the liquid organic extraction for enrichment includes the use of solid phase extraction using, e.g a Bond-Elut® column (Varian, Harbor City, Calif.) consisting of silica or fluorosil can be used to enrich for the lysophospholipid and to remove proteins and other lipids.

In order to optimize recovery of the desired lysophospholipid, inhibitors of endogenous enzymes that may be present in the sample may be used to prevent an increase in background levels of lysophospholpid or degradation of the lysophospholipid levels in the sample. Such inhibitors include specific $PLA_2$ inhibitors such as Aristolic Acid (9-methoxy-6-nitrophenanthro-(3,4-d)-dioxole-5-carboxylic acid, Biomol Research Laboratories, Plymouth Meeting, Pa.); ONO-R-082 (2-(p-Amylcinnamoyl)amino-4-chlorobenzoic acid, Biomol); OBAA (3-(4-Octadecyl)-benzoylacrylic acid, Biomol), 4-Bromophenacyl Bromide (Sigma); Quincrine (6-Chloro-9-(4-diethylamino)-1-methylbutyl)amino-2-methoxycridine, Mepacrine, Sigma); Manoalide (Biomol) and HELSS (Haloenol lactone suicide substrate, Biomol); phosphodiesterase inhibitors such as IBMX (3-Isobutyl-1-methylxanthine, CalBiochem, La Jolla, Calif.); Ro-20-1724 (CalBiochem); Zaprinast (CalBiochem) and Pentoxifylline (CalBiochem); general protease inhibitors such as E-64 (trans-Epoxysuccinyl-L-leucylamido-(4-guanidino)butane, Sigma); leupeptin (Sigma); pepstatin A (Sigma); TPCK (N-tosyl-L-phenylalanine chloromethyl ketone, Sigma); PMSF (Phenylmethanesulfonyl fluoride, Sigma); benzamidine (Sigma) and 1,10-phenanthroline (Sigma); organic solvents including chloroform and methanol; detergents such as SDS; proteases that would degrade phospholipases such as trypsin (Sigma) and thermostable protease (Boehringer Mannheim Biochemicals, Indianapolis, Ind.); and metal chelators such as EDTA (Ethylenediaminetetracetic acid, Sigma) and EGTA (Ethylene glycol-bis-(beta-aminoethyl ether), Sigma).

The assay may be performed in a microtiter plate format to permit small volumes of samples and reagents to be employed and for monitoring, e.g. using an ELISA reader. These formats facilitate automating the performance of the assay. Reduced processing times for the assays using such formats may reduce variability between results.

5.3 Correlation of Lsophospholipid Levels with Disase

Initially, physiological ("normal") concentrations of lysophospholipids and/or specific lysophospholipid species are determined in subjects not having a disease condition. Subsequently, the concentration of the lysophospholipids are measured in a sample of bodily fluid from a test subject to be screened for the disease and compared to the concentrations established for normal subjects. Concentrations of lysophospholipid that are significantly increased or decreased relative to normal controls, for example one or more standard deviations above normal, may indicate the presence of a condition associated with altered levels of the lysophospholipid.

In addition, the response of a condition to treatment may be monitored by determining concentrations of lysophospholipid in samples taken from a subject over time. The concentration of a lysophospholipid is measured and compared to the concentration taken at the earlier time from that patient. If there is an increase in the concentration of lysophospholipid over time, it may indicate an increase in the severity of the condition in the subject. Conversely, if there is a decrease in the concentration of lysophospholipid, it may indicate an improvement in the condition of the subject.

5.4 Diagnostic Kits

The methods described herein for measuring concentrations of lysophospholipids in samples of bodily fluids from a subject may also be performed, for example, by using pre-packaged diagnostic kits. Such kits include enzyme reagents for digesting one or more lysophospholipid, for example phospholipase B. The reagents include those to perform the enzyme cycling reaction such as glycerol-3-phosphate dehydrogenase, glycerol-3-phosphate oxidase and β-nicotinamide adenine dinucleotide (NADH) and ancillary agents such as buffering agents, and agents such as EDTA to inhibit subsequent production or hydrolysis of lysophospholipids during transport or storage of the samples. The kits may also include an apparatus or container for conducting the methods of the invention and/or transferring samples to a diagnostic laboratory for processing, as well as suitable instructions for carrying out the methods of the invention.

The following examples are presented to demonstrate the methods of the present invention and to assist one of ordinary skill in using the same. The examples are not intended in any way to otherwise limit the scope of the disclosure or the protection granted by Letters Patent granted hereon.

6. EXAMPLES

Example I

Detection and Quantitation of Lysopa Levels in Human Plasma

Reagents

Phospholipase B (PLB), glycerol-3-phosphate oxidase, glycerol-3-phosphate dehydrogenase, human plasma, human serum, 4-aminoantipyrine (AAP) and calcium chloride were purchased from Sigma Chemical Co., St. Louis, Mo. Lysopholipase (LYPL) was purchased from Asahi Chemical Industry, Tokyo, Japan. Peroxidase and NADH were purchased from Boerhinger Mannheim, Indianapolis, Ill. All lipid standards, fatty acids and methyl esters were purchased from Avanti Polar Lipids, Alabaster, AL or Sigma Chemical Co. 3,5 Dichloro-2-hydroxybenzenesulfonic acid sodium salt (HDCBS) was purchased from Biosynth AG, Naperville, Ill.

Sample Collection and Processing

Blood was collected in BD vacutainer tubes #6415 or #7714 utilizing a 3.2% buffered citrate (acid citrate) and maintained capped on ice until processing. Within 1 hour of draw, blood was centrifuged at 3000×g (in a cold centrifuge if possible) for 15 minutes. Plasma was removed and transferred to a plastic tube and frozen at −20°0 C. to −80° C. Alternatively, blood was drawn into EDTA-containing vacutainer tubes and centrifuged at 580×g for 5 minutes. The supernatant was transferred to a siliconized tube and centrifuged again at 8000×g for 5 mintues. The supernatant was collected into another siliconized tube and frozen at −70° C.

Sample Preparation and Thin Layer Chromatography

Approximately 0.5 ml of plasma was added to 3.75 ml of chloroform:methanol (1:2), vortexed and centrifuged at 3000 rpm for 10 minutes. The supernate was decanted into a new tube to which was added 1.25 ml chloroform and 1.75 ml water. This mixture was vortexed and centrifuged again to yield a biphasic solution. The lower layer was saved and the upper layer was collected into another tube. To this upper layer, 2.5 ml chloroform and 63 µl concentrated hydrochloric acid were added. The mixture was vortexed and then centrifuged again. The lower layer resulting from this acidified chloroform extraction was collected and pooled with the lower layer that was saved. The pooled extract volume was reduced to less than 50 µl under a nitrogen stream and spotted onto the origin of a silica gel G TLC plate (Fisher Scientific, Santa Clara, Calif.). Chromatography was performed in a solvent system containing chloroform:methanol:ammonium hydroxide (65:35:5.5).

Lipids and standards were visualized by spraying the developed plate with Rhodamine 6G (Sigma Chemical) in water and the spot corresponding to LysoPA was scraped from the plate. Each sample was spiked with heptadecanoic acid as an internal standard. The fatty acids were hydrolyzed by adding 1 ml of 1N NaOH in methanol and incubating at 100° C. for 15 minutes. After cooling, 1 ml of boron triflouride (14% in methanol, Alltech Associates, Deerfield, Ill.) was added and the sample incubated 30 minutes at room temperature to produce methyl esters. 2 ml hexane and 1 ml water were added and the mixture was vortexed thoroughly and centrifuged for 3–5 minutes at 3000 rpm to facilitate phase separation. The organic (top) layer was collected, dried under nitrogen, resuspended in 25 µl hexane and sealed in an autosampler vial.

Gas Chromatography

Fatty acid methyl esters (FAMES) were quantified using gas chromatography (GC) on a Hewlett Packard 5890 Series II GC fitted with an autosampler and flame ionization detector. 2 µl of sample in hexane were injected into a Supelco SPB-5 capillary column (Supelco, Bellefonte, Pa.). The GC program was set as follows: 170–235° C. at 10° C. per minute and then held at 235° C. for 13.5 minutes for a total run time of 20 minutes. Retention times for the methyl esters were determined using known standards and compared to peaks in unknown samples. Quantitation of peaks was performed by comparison to a heptadeconic acid standard curve using calibration against the heptadecanoic acid internal standard.

Sample Preparation For The Enzymatic Assay

Approximately 0.5 ml of plasma were added to 3.75 ml of chloroform:methanol (1:2), vortexed and centrifuged at 3000 rpm for 10 minutes. The supernate was decanted into a new tube to which was added 1.25 ml chloroform and 1.75 ml water. This mixture was vortexed and centrifuged as above to yield a biphasic solution. The upper layer was collected into another tube and 2.5 ml chloroform and 63 µl concentrated hydrochloric acid were added, the mixture vortexed and centrifuged as before. The lower layer was collected and transferred into a clean tube. The sample was evaporated completely under nitrogen and the dried lipid extract was reconstituted in 250 µl of sample buffer containing 2.5% Triton X-100, 5 mM $CaCl_2$, and 100 mM Tris (pH 8.0). The sample was stored at −70° C. until it was assayed.

Alternatively, a modified extraction procedure was developed that only utilized 100 µl of sample and significantly reduced the levels of contaminating lipids such as phosphatidylcholine and lysophosphatidylcholine. In this extraction, 0.1 ml of plasma was added to 0.75 ml of chloroform:methanol (1:2), vortexed and centrifuged at 14,000 rpm for 5 minutes. The supernate was decanted into a new tube to which was added 0.25 ml of chloroform and 0.35 ml of water. This mixture was vortexed and centrifuged as above to yield a biphasic solution. The lower layer was discarded and to the remaining upper layer was added 0.5 ml chloroform. The sample was vortexed and centrifuged again at 14,000 rpm for 5 minutes. Once again the lower layer was discarded. To the upper layer, 0.5 ml chloroform and 12.6 µl concentrated hydrochloric acid were added, the mixture vortexed and centrifuged as before. The acidified lower layer was collected and transferred to a clean tube. The sample was evaporated completely under nitrogen and reconstituted in 100 µl of sample buffer containing 2.5% Triton X-100, 5 mM $CaCl_2$, and 100 mM Tris (pH 8.0). The sample was stored at −70° C. until assayed.

Enzyme Assay

In the well of a 96 well microtiter plate, 5–100 µl of the extracted lipid sample was incubated with 0.25 units of phospholipase B or LYPL in 100 mM Tris (pH 8.0) at 37° C. for 30–60 minutes to produce G-3-P. 100 µl of cycling reaction enzyme mix containing 1.7 units of G-3-P dehydrogenase, 4 units of G-3-P oxidase, 0.25 mM NADH and 5 mM $CaCl_2$ in 50 mM Tris (pH 8.0) was added and the mixture incubated at 37° C. for an additional 60 minutes. The G-3-P oxidase converts G-3-P to dihydroxyacetone phosphate and $H_2O_2$. The dihydroxyacetone phosphate is in turn converted back to G-3-P by G-3-P dehydrogenase. This reaction oxidizes NADH to NAD. Therefore, as cycling continues, both $H_2O_2$ and NAD accumulate.

The level of LysoPA was determined by monitoring the oxidation of NADH (i.e. the reduction of absorbance at 340 nm after the cycling action compared to $A_{340}$ before cycling). In addition, the accumulation of $H_2O_2$ was determined colorimetrically by adding 50 µl of a solution containing 0.5 units peroxidase, 0.5% HDCBS and 0.15% AAP in 100 mM Tris 8.0 to each well and recording the absorbance at 505 nm.

Numerical values for concentrations of LysoPA were obtained from a standard curve constructed from known LysoPA amounts. An internal standard of extracted plasma was included within each assay (i.e. each plate) that was measured at different dilutions. In some cases, this internal standard was used to correct for variations between different experiments. Internal standards were also measured in the absence of PLB or LYPL enzyme. This "no-enzyme" sample provided a background value that was subtracted from each unknown when calculating the LysoPA levels using the NADH measurement. When the colorimetric method was used, the plate was blanked at 505 nm prior to color development.

Results

The results of the two-step enzymatic assay of the invention are shown in Table 1.

TABLE I

ENZYME ASSAY TO DETECT LYSOPA

|  | Enyzme Assay | TLC/GC Assay |
| --- | --- | --- |
| Sensitivity | 0.2 µM | 1 µM |
| Inter-assay Variability | 5% | 15% |
| Intra-assay variability | <5% | 15% |
| Yield | 90% | 10% |
| Sample Volume | 0.1 ml | 0.5–1 ml |
| Processing Time (20 samples) | 3–4 hours | 1–2 days |

These results demonstrate the advantages of the present enzymatic assay as compared to the TLC/GC assay. The assay is linear from 0.2 µM to 1 µM of LysoPA concentration. In addition, the enzymatic assays of the present invention provide high yield, increased sensitivity and rapid processing time.

Example II

Detection and Quantitation of Lysopc Levels in Human Plasma and Serum

Reagents

Lysophospholipase (LYPL) was purchased from Asahi Chemical Industry, Tokyo, Japan. Glycerophosphorylcholine phosphodiesterase (GPC-PDE), choline oxidase, and 4-aminoantipyrine (AAP) were purchased from Sigma Chemical Co., St. Louis, Mo. Peroxidase was purchased from Boerhinger Mannheim, Indianapolis, Ind. 3,5 Dichloro-2-hydroxybenzenesulfonic acid sodium salt (HDCBS) was purchased from Biosynth AG, Naperville, Ill. All lipid standards and fatty acids were purchased from Avanti Polar Lipids, Alabaster, Ala. or Sigma Chemical Co.

Sample Collection and Processing

Blood was collected and plasma was processed as described in Example I. For serum, blood was collected in silicone-coated Vacutainer tubes (Red Top) and was centrifuged under normal conditions. Serum and plasma was transferred to plastic tubes and stored frozen at −20° C. to −80° C.

Sample Preparation for the Enzymatic Assay

Approximately 35 µl plasma or serum was diluted 1:10 in sample buffer (1% Triton, 10 mM calcium chloride, 50 mM Tris pH 8.0) to a total volume of 350 µl.

Enzymatic Assay

In the well of a 96 well microtiter plate, 100 µl of the diluted lipid is aliquoted in replicate. To each well, 50 µl of LYPL (0.125 Units)/GPC-PDE (0.0125 Units) is added and incubated at 37° C. for 10 minutes. This reaction produces glycerophosphorylcholine as an intermediate through LYPL digestion of LysoPC. The GPD-PDE then liberates G-3-P and choline from glycerophosphorylcholine. The plate is then blanked A505 in the ELISA reader. Next, 50 µl choline detection mix (0.15 Units choline oxidase, 0.5 Units peroxidase, 0.03% AAP, 0.125% HDCBS, 100 mM Tris pH 8.0) is added and incubated at 37° C. for 15 minutes. The plate is then read at $A_{505}$.

Table II illustrates the results of the assay for LysoPC. The assay is linear from 5 to 200 µM LysoPC, sensitive to 5 µM LysoPC and exhibits low intra-assay and inter-assay variability.

TABLE II

Enzyme Assay to Detect LysoPC in Plasma

| | |
|---|---|
| Sensitivity | 5 µM |
| Linear Range | 5–200 µM |
| Intra-assay Variability | 3.0% |
| Inter-assay Variability | 6.0% |

These results show that LysoPC is easily detected in plasma or serum using the two-step enzyme assay of the invention. Similar results were obtained from plasma or serum from the same patient, demonstrating that the method is applicable to either plasma or serum. Typical LysoPC levels in plasma or serum ranged from 50 µM to 500 µM. As a result, LysoPC can be determined in a 1:10 diluted sample using this assay.

Example III

Detection and Quantitation of Lysopa in Samples from Patients Having Cancer

LysoPA levels were determined in plasma of both non-cancer subjects and patients having ovarian cancer. Blood was collected from female patients and was processed as described above in Example I. Plasma from the samples was prepared for the enzymatic assay of the invention as described above in Example I. The enzyme assay was performed as described above in Example I.

Average LysoPA levels for non-cancer and cancer patients as determined using the enzyme assay. Shows that average levels of LysoPA were significantly increased in the plasma of patients having ovarian cancer as determined using the methods of the invention.

In addition, levels of LysoPC and PC were determined from the plasma of patients with and without ovarian cancer using the enzyme assay as described above in Examples II and III. These results were combined and multiplied to yield a multi-lipid diagnostic measurement. Levels of LysoPC and PC determined independently were 10 to 100% higher in ovarian cancer versus normal patients. Combining and multiplying LysoPA X LysoPC X PC levels for each sample yielded a measurement from 400% to 500% higher in ovarian cancer versus normal patients. These results suggest that the combinatorial approach may provide a more accurate assay for detecting conditions such as cancer associated with altered levels of lysophospholipids and phospholipids by reducing the number of false positive and false negative results.

Example IV

Detection and Quantification of Lysopa in Patients Having a Bleeding Disorder

LysoPA levels were determined as described above in Example I in 93 plasma samples from male and female patients over an age range of 1–80 years. Of the 93 samples, 17 of samples came from patients who were previously diagnosed with bleeding disorders (i.e. coagulopathy). LysoPA levels were determined. Patients having a bleeding disorder demonstrated significantly higher average LysoPA levels than those patients not having cancer or a bleeding disorder.

The results from the examples herein demonstrate that the methods of the invention can be used to detect altered lysophospholipid and phospholipids such as PC levels in patients having various disease conditions associated with such altered levels. Moreover, these results provide a new method for diagnosing disease conditions associated with altered levels of lysophospholipids in which levels of different phospholipids such as LysoPA and LysoPC in plasma or serum are multiplied to detect the disease condition.

Various publications are cited herein which are hereby incorporated by reference in their entirety.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

What is claimed is:

1. A method to detect a disease condition in a subject comprising:
    digesting lysophosphatidic acid in a sample of bodily fluid from the subject with a first enzyme to produce substrate;
    reacting the substrate with a second enzyme in an enzymatic cycling reaction to produce a detectable product;
    determining the concentration of lysophosphatidic acid by measuring the detectable product; and
    correlating the concentration of lysophosphatidic acid to the disease condition by comparison to a normal concentration.

2. The method of claim 1, wherein said first enzyme is selected from the group consisting of phospholipase B, lysophospholipase, phospholipase $A_1$, and phospholipase $A_2$.

3. The method of claim 1, wherein the second enzyme is selected from the group consisting of glycerol-3-phosphate dehydrogenase, glycerol-3-phosphae oxidase, glycerokinase and glycerol dehydrogenase.

4. The method of claim 1, wherein the substrate is glycerol-3-phosphate.

5. The method of claim 1, wherein the detectable product is hydrogen peroxide.

6. The method of claim 5, wherein the step of determining the concentration of lysophosphatidic acid by measuring detectable product comprises measuring an increase in hydrogen peroxide by colorimetry.

7. The method of claim 1, wherein the detectable product is NADH.

8. The method of claim 7, wherein said step of determining the concentration of the lysophosphatidic acid by measuring the detectable product comprises measuring oxidation of NADH.

9. The method of claim 1, wherein the step of reacting the substrate in an enzyme cycling reaction comprises reacting G-3-P with glycerol-3-phosphate dehydrogenase and glycerol-3-phosphate oxidase.

10. The method of claim 1, wherein, the sample of bodily fluid is selected from the group consisting of plasma, serum, urine, saliva, ascites, cerebral spinal fluid and pleural fluid.

11. The method of claim 1, further comprising the step of extracting lipids from the sample of bodily fluid.

12. The method of claim 1, firther comprising the step of conparing the concentration of lysophosphatidic acid with an earlier concentration from the same subject.

13. The method of claim 1, wherein an increase or decrease in the concentration of lysophosphatidic acid relative to normal subjects indicates the presence of the disease condition.

14. The method of claim 1, wherein the disease condition is gynecological cancer or ovarian cancer.

15. The method of claim 1, wherein the disease condition is a blood disorder associated with alteration in the level of lysophophatidic acid.

16. A method to detect a disease condition by measuring lysophosphatidic acid comprising:

digesting lysophosphatidic acid in a sample of bodily fluid wit a first enzyme to produce glycerol-3-phosphate;

reacting the glycerol-3-phosphate in an enzymatic cycling reaction;

determining the concentration of lysophosphatidic acid by measuring oxidation of NADH or accumulation of hydrogen peroxide; and correlating the mcasurement of NADH oxidation or hydrogen peroxide accumnulation with the presence of the disease condition.

17. The method of claim 16, wherein the first enzyme that digests the lysophosphatidic acid is selected from the group consisting of phospholipase B and lysophospholipase.

18. The method of claim 16 wherein the enzymatic cycling reaction is comprised of reacting G-3-P with glycerol-3-phosphate dehydrogenase and glycerol-3-phosphate oxidase.

19. The method of claim 16, wherein said disease condition is a gynecological cancer.

20. The method of claim 19, wherein the gynecological cancer is ovarian cancer.

* * * * *